(12) United States Patent
Sagrado

(10) Patent No.: US 11,089,794 B2
(45) Date of Patent: Aug. 17, 2021

(54) METHOD AND COMPOSITION FOR PREPARING A THERAPEUTIC NATURAL TEA REMEDY FOR HELPING THE HUMAN BODY COMBAT THE EFFECTS OF VARIOUS MEDICAL AILMENTS

(71) Applicant: Sagrado Natural Tea Remedies, Woodstock, IL (US)

(72) Inventor: Ramon Sagrado, Woodstock, IL (US)

(73) Assignee: Sagrado Natural Tea Remedies, Inc., Woodstock, IL (US)

( * ) Notice: Subject to any disclaimer, the term of this patent is extended or adjusted under 35 U.S.C. 154(b) by 37 days.

(21) Appl. No.: 16/475,187

(22) PCT Filed: Dec. 31, 2017

(86) PCT No.: PCT/US2017/069144
§ 371 (c)(1),
(2) Date: Jul. 1, 2019

(87) PCT Pub. No.: WO2018/126235
PCT Pub. Date: Jul. 5, 2018

(65) Prior Publication Data
US 2019/0335782 A1    Nov. 7, 2019

Related U.S. Application Data

(60) Provisional application No. 62/441,204, filed on Dec. 31, 2016.

(51) Int. Cl.
| | | |
|---|---|---|
| A23F 3/14 | (2006.01) | |
| A23F 3/18 | (2006.01) | |
| A61K 9/00 | (2006.01) | |
| A61K 9/06 | (2006.01) | |
| A61K 36/22 | (2006.01) | |
| A61K 36/30 | (2006.01) | |
| A61K 36/37 | (2006.01) | |
| A61K 36/48 | (2006.01) | |
| A61K 36/60 | (2006.01) | |
| A61K 36/61 | (2006.01) | |

(52) U.S. Cl.
CPC .................. *A23F 3/14* (2013.01); *A23F 3/18* (2013.01); *A61K 9/0014* (2013.01); *A61K 9/06* (2013.01); *A61K 36/22* (2013.01); *A61K 36/30* (2013.01); *A61K 36/37* (2013.01); *A61K 36/48* (2013.01); *A61K 36/60* (2013.01); *A61K 36/61* (2013.01)

(58) Field of Classification Search
None
See application file for complete search history.

(56) References Cited

U.S. PATENT DOCUMENTS

2009/0104295 A1    4/2009 Kohno

OTHER PUBLICATIONS

International Search Report, PCT Pat. App. No. PCT/US2017/069144.
Written Opinion of the International Searching Authority, PCT Pat. App. No. PCT?US2017/069144.
Shiva et al. Sappan Wood Herbal Green Tea:, Nov. 23, 2016, Priya Kitchenette, pp. 1-6.
Kim, "Narra Tree Medicinal Properties of its Herbal Tea", 2009, Environmental Challenges of the RP, pp. 1-5.
Langenberger et al. "Ethnobotanical knowledge of Philippine lowland farmers and its application in Agroforestry", May 2009, Agroforestry Systems, vol. 76(1), pp. 173-194.
"Biancaea sappan", Nov. 7, 2016, Wikipedia, p. 1-2.

*Primary Examiner* — Katherine Peebles
(74) *Attorney, Agent, or Firm* — Scherrer Patent & Trademark Law, P.C.; Stephen T. Scherrer; Monique A. Morneault

(57) ABSTRACT

Therapeutic tea remedy mixtures in the form of beverages and ointments. Methods for making the tea remedy mixtures are described along with the benefits it provides to combat various medical ailments that frequently impair the human body.

13 Claims, No Drawings

METHOD AND COMPOSITION FOR PREPARING A THERAPEUTIC NATURAL TEA REMEDY FOR HELPING THE HUMAN BODY COMBAT THE EFFECTS OF VARIOUS MEDICAL AILMENTS

FIELD OF THE INVENTION

The present invention relates to a therapeutic tea remedy mixtures, specifically including beverages and ointments made therefrom. Methods for making the tea remedy mixtures are described along with the benefits it provides to combat various medical ailments that frequently impair the human body.

BACKGROUND OF THE INVENTION

Therapeutic tea beverages are well known in the art and have been produced for decades and potentially centuries. Typically, tea beverages derive from tea leaves, either single source or combinations of several tea plants in various stages of maturation; leaves are typically classified as green, white, or black. According to literature, tea beverages have also been produced by boiling and extracting functional compounds from other parts of plant materials such as; roots, seeds, bark, fruit and flowers. Southeast Asia has been a great outlet of such natural remedies for centuries. In this present Invention, a unique combination of plants has been identified to prepare a custom tea blend to combat various ailments that frequently impair the human body.

BRIEF DESCRIPTION OF THE INVENTION

A natural tea remedy which has properties for treatment and also prevention of various ailments has been identified. It is prepared by blending 7 distinct tree branch ingredients procured from the forests of the Philippines. The natural tea remedy of the present invention may be utilized to maintain the health of individuals and organs of the individuals, such as, for example, skin conditions for perspiration and to fight topical infections, liver for detoxification of food, brain for proper cognitive function and retaining memory, lungs for respiration and energy, heart for cardiovascular stability including proper blood pressure and minimizing or reducing heart attacks and strokes, kidney for detoxification of urine, stomach and intestines for proper digestion and absorption of nutrients, including immunological benefits for preventing cancer. The present invention has an extensive set of ingredients which provides multiple benefits as it will be illustrated in this document for each of the ingredients as well as testimonials from people who have consumed the tea remedy.

Typically natural tea remedies have unique properties, one of the most common and important one is functioning by removing from the human body toxic materials which initiate cancers, promote cancers, and accelerate cancers. Teas naturally high in polyphenols and flavonoids such as catechins with unique combinations of the same have been documented to increase the natural immunity of the blood and increase the cancer fighting properties by elevating the level of antioxidants which promote good blood circulation and eliminate free radicals found in the human body. The specific 7 tree components at the ratios described later in this document provides many benefits. The benefits are significantly more extensive than traditionally seen in teas which offer one or two benefits. In addition, the natural tea remedies of the present invention provide new benefits which had not been seen before by consumption of each of the tea ingredients alone; it is highly probable that synergistic effects are taking place by combining the plant ingredients. Note that Mr. Ramon Sagrado is not a medical doctor and administration of the tea remedy was done in good faith. If patients were taken prescribed medication, Mr. Ramon Sagrado did not advise them on modifying any of their doctor's procedures or treatments. The Sagrado Natural Tea Remedy was taken in addition to any other treatment (if any) the patients had been taken.

For many decades it has been understood and proven by science that polyphenols such as catechins have antioxidant properties. Catechins are found in the natural tea remedies of the present invention in a unique combination which may very well exhibit synergistic effects therefore providing multi-modes of actions to combat such ailments and unbalances of the body organ systems identified above. These plant metabolites belong to the group of flavan-3-ols commonly known as flavanols. It has been established that the name of the catechin chemical family is derived from the catechu, which is the tannic juice or boiled extracts. The natural tea remedies of the present invention are essentially prepared by boiling at least two of the 7 unique tree branch and twig ingredients. As stated above, polyphenols, more specific, flavonoids have antioxidant activity, the catechin family has been found to be strong scavengers of free radicals which cause disease such as cancer.

Traditional herbal medicine from various parts of the world including those of the Philippines have been well documented for many decades, perhaps centuries of combating ailments of various types of disease including those associated with cancer, arthritis, diabetes, cardiovascular, immunological, gastrointestinal and others. In this invention, a mixture of at least two of the seven distinct tree plants has been prepared as a therapeutic tea remedy to help individuals with diagnosed diseases or even mild discomforts which trouble them and keep them from having a normal healthy life. This unique mixture serves well to address abnormalities or disease associated the body's main organ systems. In this invention, several first hand testimonials were collected from individuals whom have voluntary reported as having positive outcomes from consuming the natural tea remedies of the present invention. The reported advantages go beyond a single or a dual benefit. The unique combination of these plant materials provides a complete package to maintain a more full balance of the human body.

The object of the present invention is implemented in four essential steps for the preparation and administration of the natural tea remedies of the present invention.

First, the procurement of the unique 7 ingredients is currently obtained from the Philippines with guidance from the native Subanens tribes. The location is from the forests and mountain ranges of Malindang in the province of Misamis Occidental. A list of such plant ingredients is disclosed later in this document.

Second, the preparation of the wood chips from the 7 plant sources is described. A portion from each of the tree branches in unique proportions are the necessary components for producing the Sagrado Natural Tea Remedy.

Third, the preparation of the tea concentrate is described. This procedure is associated with boiling the wood chips (tree branch materials) in potable water to extract the active ingredients within the plants. The procedure as described in the detail description of the invention.

The fourth and final step is the oral administration of the tea remedy. In most cases, one tablespoon of the tea concentrate is mixed with the user's favorite beverage, it can be plain water, juice, coffee or a similar beverage. Typically, the consumption is done once per day, for a period of about 2 months or until suggested depending on the type and severity of the condition. In some cases the tea remedy is consumed not necessary to combat an ailment but to maintain the body in balance and to prevent the onset of a disease.

DETAIL DESCRIPTION OF THE INVENTION

A natural tea remedy which has properties for preventing and diminishing various ailments has been identified. It is a combination of several natural plants. It is prepared by blending 7 distinct tree branch ingredients procured from the forests of the Philippines. The Philippine native Subanens Indians, a tribe whom have practiced such procedures from traditional natural medicines and remedies for centuries. Such natural teas have aided with ailments of many sorts of dieses including but not limited to the treatment of cancers of various types, such as; leukemia, mammary cancer, bone cancer, pancreatic cancer, liver cancer, bladder cancer, skin cancer, and other types. These types of natural tea remedies have diverse properties that function by removing from the human body toxic substances which can initiate cancers, promote cancers and or accelerate cancers. Teas naturally high in polyphenols and flavonoids such as catechins with unique combinations of the same have been documented to increase the natural immunity of the blood and increase the cancer fighting properties by elevating the level of antioxidants which promote good blood circulation and eliminate free radicals found in the human body. By combining the 7 specific tree components at the ratios described later in this document has proven to offer many benefits from natural functional components found in the plant ingredients.

For many decades it has been understood and proven by science that polyphenols such as catechins have antioxidant properties. Polyphenols are found in the natural tea remedies of the present invention. Specifically, catechins are found in the tea remedy. Although the catechins may not be as high as in the traditional herbal teas, the unique combination may very well be exhibiting synergistic effects therefore providing multi-mode of actions to combat multiple ailments. The fact that 7 distinct plant materials are blended to produce the natural tea remedies of the present invention provides a more complete set of benefits than traditional herbal remedies which are singular or a blend of 2 or 3 ingredients. A common analogy is known in the Artistic world with paintings with a message along this way; It is not only the amount of paint or the number of colors to create a masterpiece that matters, what really matters is the effect or impact of the unique and exquisite combinations of such colors on the final product and impact on the eye of the beholder. In the case of the natural tea remedies of the present invention, it is believed that it offers a broader range of benefits which can alleviate certain ailments but also can maintain the main organ systems of the body healthy and prevent the ailments from occurring. It is highly probable that synergistic effects are taking place by combining the 7 plant ingredients as seen in the obtained testimonials.

From a historical perspective, the knowledge and associated benefits of such tree branch materials has been known and passed for generations, but never before seen in this format and combination as presented in this invention, and as effective as it has been experienced by persons consuming the natural tea remedies of the present invention over the recent months. These plant secondary metabolites belong to the group of flavan-3-ols commonly known as flavanols. It has been established that the name of the catechin is derived from the word catechu, which is the tannic juice or boiled extracts. The natural tea remedies of the present invention are essentially prepared by boiling the unique tree branch and tree twig combinations. FIG. 1 is that of a catechin which contains two benzene rings referred to as the A and the B benzene rings. The third ring C is referred as the dihydropyranheterocycle with a hydroxyl group on carbon 3. If there are two chiral centers on the molecule on carbon 2 and carbon 3, then, it is referred as having four diastereoisomers, two being the Trans type which are the catechins and the other two being the Cis type which are referred as epicatechins. As stated above, polyphenols, more specific, flavonoids have antioxidant activity. The catechins are a type of flavonoids that exist in nature, they have been found to be strong scavengers of free radicals. The free radicals in the body cause many issues including abnormalities which can lead to cancer.

An article written by Pietta, P. G. in 2000, "Flavonoids as antioxidants" published in the Journal of Natural Products 63 (7), states that the ability for single oxygen quenching appears to be in associated with the chemical structure of the catechin. Having the catechol moiety on the B ring and the hydroxyl group activating the double bond on the C ring makes the quenching possible.

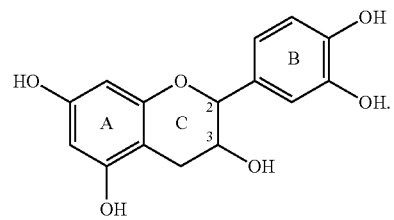

FIG. 1

The catechin profiles as well as other chemical composition of the natural tea remedies of the present invention are listed later in this document in table 3. Testing was conducted and results reported by an international accredited Testing Laboratory, Covance Inc., based in Princeton, N.J.

The natural tea remedies of the present invention are therapeutic natural teas which indicate to be effective to combat several ailments inclusive of having anti-cancer properties found in catechins. Various types of cancer tumors initiate a destructive, degenerative effect on the human body. The natural tea remedies of the present invention, as testified by some people below, has shown the ability to inhibit the production of cancer tumors or to destroy them once initiated. In recent decades, there have been many studies published as to what is causing cancer. It has been established that the onset of the industrial revolution has led to many environmental pollutants which can very well be linked to the increase of cancer in first and second world countries. Although today, there are options to fight such cancers via chemotherapy, radiation and other forms of pharma modes, ancient ancestors have pointed out that nature can offer some more humane and gentle pathways to combat such diseases. The inventor of the natural tea remedies of the present invention, a native of the Philippines has gathered and compiled a unique combination of several trees branch materials which have existed in the Philippines for centuries. It is also critical to state that through the years, earlier generations have shared a wealth of knowledge to arm new generations with ammunition which is derived from mother earth, the knowledge has been passed in many ways including via therapeutic home remedies to treat such ailments with minimal or no negative side effects when compare to current pharma choices.

The object of the present invention is to provide a more simple, yet effective method for the production of the therapeutic natural tea remedies which are consumed orally and has been effective in the treatment of several ailments as it will be described later in this document via first hand notarized written testimonials as well as oral testimonials from real life experiences.

The object of the present invention is implemented in four unique and essential steps for the preparation and administration of the Sagrado Natural Tea Remedy.

First

The procurement of the 7 unique ingredients is currently obtained within the Philippines. Location is within the forests and mountain ranges of Malindang in the providence of Misamis Occidental. The 7 unique plant ingredients are as follows:
1. Bulungan Balagon (*Celastrus urbiculatus*)
2. Duguan (*Myristica philippinensis*)
3. Narra, Rosewood (*Pterocarpus indicus*)
4. Balitarhan (*Ficus codatula* var. *sericea*)
5. Anonang (*Corida dickhotoma*)
6. Sapan Wood, heartwood (*Caesalpinia sappan*)
7. Luyan Luyan, (*Dracontomelon dao*)

There has been substantial common knowledge of these plants, they have been used by centuries by the native tribes, the Subanens Indians in the Philippines, have practiced such procedures by relaying on traditional therapeutic natural medicines and remedies for centuries. Such common knowledge obtained by ancestors as well as published scientific work done by various researchers indicates significant health benefits. Such natural teas have aided with ailments of many sorts of health conditions including but not limited to cancer as well as other health benefits from cited research in the area of arthritis, gastrointestinal, cardiovascular, respiratory, perspiration, detoxification and diabetes amongst others.

More specifically, for each of the 7 plants, the individual benefits have been outlined as follows. But, before each isolated plant is reviewed, the notion that synergistic effects are taking place has been evident by the various testimonials listed in this invention.
1. Common knowledge for Bulungan Balagon (*Celastrus urbiculatus*), also known as Oriental bittersweet, indicates that it has historically been used for many benefits including but not limited to the treatment of inflammations, rheumatoid arthritis, having detoxifying effects, as an anti-paralysis, prevents numbness of the extremities, eliminates spontaneous abscess formation, for treating cancer, as a diuretic and for treating snake bites.
2. Common knowledge for Duguan (*Myristica philippinensis*), a member of the nutmeg family, indicates that it has historically been used for many benefits including but not limited to the treatment for normalizing menstrual cycles in women, normalizes body temperature in people with fevers specifically children with a high temperature due to measles, treatment of cancer of woman's reproductive organs.
3. Common knowledge for Narra, Rosewood (*Pterocarpus indicus*), also known as Philippine mahogany, indicates that it has historically been used for many benefits including but not limited to the treatment of several cancerous tumors from various sources, to treat diabetes mellitus, kidney problems such as kidney stones, celiac disease, a disease of the small intestine.
4. Common knowledge for Balitarhan (*Ficus codatula* var. *sericea*), which is also seen with other species of the genus *Ficus*, indicates that it has historically been used for any benefits including but not limited to the treatment and prevention of various cancers, it reduces cholesterol, prevents high blood pressure which can lead to heart attacks and other cardiovascular issues, it helps cure diabetes, provides energy, reduces fatigue, prevents anemia, treats constipation and treats hemorrhoids.
5. Common knowledge for Anonang (*Corida dickhotoma*), also known as clammy cherry, indicates that it has historically been used for many benefits including but not limited to the treatment and prevention of digestive discomfort, as an analgesic, an anti-inflammatory, an anti-oxidant which can prevent cancer, an expectorant, an anti-arthritic, treats dyspepsia, diarrhea, dysenteric fever, headaches, and stomach aches.
6. Common knowledge for Sapan wood, Heartwood (*Caesalpinia sappan*), also known as Su Mu, indicates that it has historically been used for many benefits including but not limited to the treatment and prevention of anemia, arthritis, is used as a blood purifier, treats acne, its an anti-bacterial, an analgesic, improves blood circulation, prevents gynecological disorders, it has anti-inflammatory and strong antioxidant activity to provide benefits against cancer.
7. Common knowledge for Luyan Luyan, (*Dracontomelon dao*), also known as dao, papua, Pacific walnut indicates that it has historically been used for many benefits including but not limited to the treatment and prevention of ulcers, as an antidote for poisoning, prevents dysentery, cures sore throat, prevents inflammation.

Second

The next essential step is the preparation of the wood chips from the 7 tree plant materials. Table 1, has the essential steps for preparing the plant materials to produce the Sagrado Natural Tea Remedy.

TABLE 1

| Wood Chips Preparation |
|---|
| 1 Locate seven (7) distinct trees of mature age |
| A 35 years of age or greater |
| B In good botanical condition |
| C From the specific geographical location listed above |
| D From the specific genius and spices listed above |
| 2 Cut branches from each distinct tree |
| A Branches to be segregated by tree type |
| B Branches to be approximate 4 to 10 centimeters in diameter |
| C Keep branches in a dry and cool area after removing from tree |
| 3 Chop branches by tree type into wood chips |
| A Size of wood chips to be approx. 2 to 4 centimeters in length |
| B Is fine for wood chips to include the bark portion |
| C Wood chips to be free from any disease, rot or insects |
| 4 Dry wood chips |
| A Maintain segregation of each tree type |
| B Typically sun dried for approximately 2-3 days |
| 5 Wood chips storage |
| A Package in large plastic bags. Approximately 5 to 10 Kilos per bag |
| B Seal each bag, preferably with air removed |
| C Store bags in dry area, room conditions is fine but preferably cool |

Third

The third essential step is the preparation of the natural tea remedies of the present invention as a concentrate. This procedure in captured in Table 2 below. The procedure is only an indication for an example for preparing a small batch of tea concentrate. Proportions will maintain constant once larger batches are produced

TABLE 2

Preparation of the Tea Concentrate

| | |
|---|---|
| 1 | Combine all seven wood chip types at levels of 1% to 80% each by weight. More preferably at levels of 3% to 50% each by weight. Even more preferably at levels of 5% to 20% each by weight. For a small batch or personal size batch, it would consist of approximately 210 grams of combined wood chips |
| 2 | Place wood chip mixture into metal pot, add 2.5 liters of tap (potable) water |
| 3 | Bring chips and water mixture to a boil on a stovetop and let boil at medium flame, uncovered for 1 hr. At end of preparation, the mixture will yield approximately 2.25 liters of Tea Concentrate |
| 4 | Filter mixture through common kitchen sieve to remove chips, bark and other large visible solids |
| 5 | Cover pot with lid and let tea liquid cool off to room temperature |
| 6 | Pour tea into 1 liter glass or heat protective bottles or containers. Apply production sticker; product name, production date, contents and contact information. |
| 7 | Store tea concentrate bottles at refrigerated conditions (5° C. or 35° F.) until time of consumption |
| 8 | Consume tea as directed. Consumption procedure varies depending on severity and type of ailment |
| 9 | Keep refrigerated while consuming the tea until 1 liter container is finished or as directed |
| 10 | Shelf life of tea is currently 2 months after opening. Note, no preservatives or other additives are being added to the tea concentrate |

In a commercial setting, the natural tea remedy concentrates of the present invention would be prepared in a similar fashion as outlined in Table #2 but using commercial grade pasteurizers and common conditions known to one skilled in the art. Typical setting can include but not limited to Batch Processing or LTLT (low temperature, long time) of 145 F for 30 minutes. HTST (high temperature, short time) of 161 F for 15 seconds. HHST (high heat, short time) of 191 F for 1 second. Other thermal treatments and non-thermal treatments can also be applicable depending on the available equipment, storage temperature and desired shelf life. To prolong the shelf life even longer, stabilizers, preservatives or other additives can also be considered.

Alternatively to full preparation of the natural tea remedy concentrates of the present invention, the inventor can also offer the same ultimate benefits to the product to human users by providing the tree branch wood chip ingredients in a dry form; potentially in a tea bag or similar and also provide the specific preparation instructions to consumers. This format may be more beneficial and easier to access by users in remote locations of the world.

Fourth

The fourth and final step is the administration of the natural tea remedies of the present invention. In most cases, each user consumes one tablespoon of the tea concentrate mixed with the user's favorite beverage, it can be plain water, fruit juice, coffee or similar beverage. Typically, the consumption is done once per day, for a period of about 2 months or until suggested or until a one liter container is completely consumed. Note that each user is unique and the dose for each user may vary depending on type or severity of ailment.

The catechin profile as well as other chemical composition of the natural tea remedies of the present invention is listed below in Table 3. Product testing and profiling was conducted by an international accredited Testing Laboratory, Covance Inc., based in Princeton, N.J., a contract research organization which provided the testing services. The chemistry results illustrated in Table 3 are a single set of results for a composite of 12 lots (distinct batches) of the natural tea remedies of the present invention in the form of a beverage.

TABLE 3

Chemistry Profile of the Sagrado Natural Tea Remedy concentrate

| | |
|---|---|
| Covance Report # | 1470669-0 |
| Report Date | 08 Apr. 2016 |
| Report Status | Final |
| Client | Sagrado Natural Tea Remedies, Woodstock Illinois 60098 United States |
| Sample Name | Sagrado Natural Tea Remedy |
| Sample Type | Tea Product |
| Covance Sample: | 4866814 |
| Project ID | SAGRADO_NA-20160330-0001 |
| Receipt Date | 30 Mar. 2016 Receipt Condition Ambient temperature |
| Login Date | 30 Mar. 2016 Storage Condition 5 (+/−3) degrees Celsius |
| Order Analysis Results: | |
| Calories | 2.22 Cal/100 g |
| Calories from Fat | <1.00 Cal/100 g |
| Fat by Acid Hydrolysis | <0.1 g/100 g |
| Carbohydrates | 0.2 g/100 g |
| Sugar Profile: | |
| Fructose | <0.1 g/100 g |
| Glucose | <0.1 g/100 g |
| Sucrose | <0.1 g/100 g |
| Lactose | <0.1 g/100 g |
| Maltose | <0.1 g/100 g |
| Galactose | <0.1 g/100 g |
| Total Sugar | <0.1 g/100 g |
| Protein (N × 6.25) Dumas Method | 0.30 g/100 g |
| Vitamin A as Retinol | <100 IU/100 g |
| Vitamin C | <1.0 mg/100 g |
| Elements by ICP Emission Spectrometry: | |
| Calcium | 8.97 mg/100 g |
| Copper | 0.0149 mg/100 g |
| Iron | 0.0436 mg/100 g |
| Magnesium | 5.42 mg/100 g |
| Manganese | 0.0443 mg/100 g |
| Phosphorus | 6.44 mg/100 g |
| Potassium | 43.3 mg/100 g |
| Sodium | 2.52 mg/100 g |
| Zinc | 0.0131 mg/100 g |
| Ash | <0.100 g/100 g |
| Moisture | 99.5 g/100 g |
| Ph | 5.98 |
| Catechins: | |
| Epigallocatechin | 2.09 mg/100 g |
| Catechin | <0.100 mg/100 g |
| Epicatechin | 1.00 mg/100 g |
| Epigallocatechin Gallate | 0.686 mg/100 g |
| Gallocatechin Gallate | <0.100 mg/100 g |
| Epicatechin Gallate | <0.100 mg/100 g |
| Gallocatechin | <0.100 mg/100 g |
| Catechin Gallate | <0.100 mg/100 g |
| Total Catechins | 3.78 mg/100 g |
| Total Polyphenols | 121 mg/100 g |
| Elements by ICP Mass Spectrometry: | |
| Arsenic | <1.00 mcg/100 g |
| Cadmium | <1.00 mcg/100 g |
| Lead | <0.500 mcg/100 g |
| Mercury | <1.00 mcg/100 g |
| Color: | |
| L Value | 8.24 |
| a Value | 6.79 |
| b Value | 11.59 |

To confirm that the efficacy of the natural tea remedy concentrates is fully effective every single dose for delivering the benefits listed above, an experiment was conducted utilizing a set of tree branch wood chips following the preparation procedure listed in step #3. The experiment consisted of performing the extraction of the bioactives off the same set of tree branch wood chip ingredients three times. Samples of the tea concentrate were collected after the fist, the second and the third boiling extraction. Samples were then submitted to the Covance Laboratory for analysis specifically to obtain the levels of total catechins and total polyphenols.

Table 4 below captures the levels as analyzed. Based on these set of results, only one boiling of the tree branches wood chip ingredients is conducted to ensure full efficacy and full benefits are delivered every single time.

TABLE 4

Chemistry Profile of the Sagrado Natural Tea Remedy concentrate after three consecutive boiling were conducted on same set of tree branch wood chips.

| | |
|---|---|
| Covance Report #s | 1784531-0, 1785304-0, 1785305-0 |
| Report Dates | 10 Apr. 2017, 11 Apr. 2017, 11 Apr. 2017 |
| Report Status | Finals |
| Client | Sagrado Natural Tea Remedies, Woodstock Illinois 60098 United States |
| Sample Name | Sagrado Natural Tea Remedy |
| Sample Type | Tea Products |
| Covance Samples: | 6008602, 6008603, 6008604 |
| Project ID | SAGRADO_NA-20170330-0001 |
| Receipt Date | 30 Mar. 2017 Receipt Condition Ambient temperature |
| Login Date | 30 Mar. 2017 Storage Condition 5 (+/−3) degrees Celsius |
| Order Analysis Results: | |
| Total Catechins $1^{st}$ extraction | 5.54 mg/100 g |
| Total Catechins $2^{nd}$ extraction | 1.62 mg/100 g |
| Total Catechins $3^{rd}$ extraction | 0.508 mg/100 g |
| Total Polyphenols $1^{st}$ extraction | 130 mg/100 g |
| Total Polyphenols $2^{nd}$ extraction | 56.5 mg/100 g |
| Total Polyphenols $3^{rd}$ extraction | 28.2 mg/100 g |

Testimonials

For the natural tea remedies of the present invention, several first hand testimonials have been voluntarily provided and collected from individuals whom have testified. These individuals have obtained a benefit from the consumption of the natural tea remedies described herein. All written testimonials have been completed and signed by the person obtaining the benefit and documents have been officially notarized. The Sagrado Natural Tea Remedy has helped many individuals in both Eastern and Western global hemispheres; North America, specifically in the US in the state of Illinois as well as many individuals in Asia, specifically in the Philippines in the area of Misamis Occidental.

There are also several verbal testimonial were also separately acquired and provided by the person obtaining the benefit directly to the inventor.

The following are some of the summarized benefits obtained from the testimonials provided by several people whom have taken the natural tea remedies of the present invention under confidentiality. Note that the inventor is not a medical doctor and administration of the tea remedy was done in good faith. If patients were taken prescribed medication, the inventor did not advise them on modifying any of their doctor's procedures or treatments. The natural tea remedies as described herein were taken in addition to any other treatment (if any) the patients had been taken.

Written and Notarized Testimonials:

Maureen M. a resident in the state of, Illinois, USA, was diagnosed with type I diabetes in 2007, since then, her medical doctor prescribed Novolog insulin, which she began to take daily via injections. After taking the insulin, her sugar levels were improved and controlled but she continuously felt tired, sluggish and bloated for many years. In January of 2016, Maureen started consuming a natural tea remedy of the present invention once per day (1 teaspoon of the tea concentrate mixed with one glass of water), one week after taking the tea, she noticed significant improvement with her health. "Began to feel good, more energy, no more bloating" and decreased insulin from the daily prescribe level of 32 units to 27 units.

Gary T. a resident of the state of Illinois, USA, was diagnosed with high blood pressure in 2012. He had constant fatigue and unexplained weight gain. His primary doctor put him under prescribed medication Diovan. After taking the prescribe medication, his cardiovascular conditions slightly improved, he felt a bit better. In May of 2016, Gary started consuming a natural tea remedy of the present invention once or twice per day (2 teaspoons of the tea concentrate mixed with one glass of water). After taking the tea remedy for a period of 10 weeks, he noticed significant improvement with his health. The high blood pressure had significantly improved, energy level increased and the challenge with his weight was corrected and now has loss several pounds.

Jose R. a resident of the state of Illinois, USA, had constant fatigue on a daily basis. Felt tired, Jose consulted with his primary doctor and was prescribed medication to help his energy level along with vitamin supplements. He took the prescribed pills for several months and did not feel a significant difference in improving his constant fatigue condition. He then obtained a natural tea remedy from the inventor and started taking the tea remedy as recommended. Jose states that approximately two weeks after consumption of the tea on a daily basis (1 teaspoon of the tea concentrate mixed with one glass of water) he started to feel much better. Tea provided strength and energy to go about his day without slowing down.

Meggie R. a resident of the state of Illinois, USA, had chronic cough, she would cough vigorously and constantly on a daily basis and had done it for many years. She had gone to see two different medical doctors for this condition and was unsuccessful to better her coughing condition. Each doctor prescribed different pharmaceuticals, antibiotics and none had any significant success in making her feel better. She then took a natural tea remedy of the present invention. After consuming the Sagrado tea concentrate (1 teaspoon of the tea concentrate mixed with one glass of water) for three weeks, she stated that approximately 80% of the cough subsided. Now the cough is nowhere as vigorously or as constant as it used to be.

Margarita R. a resident of the state of Illinois, USA, was diagnosed with type I diabetes in 1993, she was prescribed insulin by her endocrinologist doctor. Since then she has been takin 3 insulin injections per day. Each year she goes to her endocrinologist for a physical assessment, during the past 10 years, her hemoglobin A1C value had been in the range of 6.8 to 6.9. Margarita was recommended to consume the natural tea remedy of the present invention. In June 2015, she began to take the tea remedy (2 teaspoons of the tea concentrate with a glass of water per day). After taking the tea for about 3 weeks, she began to feel more energized. During the annual assessment of her diabetic conditions in 2016, her endocrinologist noted a very significant drop in her hemoglobin A1C, the levels dropped from 6.9 to 6.4, Margarita continued to feel better and energized enough where she has now joined a local workout gym.

Ted R. a resident of the state of Illinois, USA, had chronic arthritis and fibromyalgia for the past 7 years. He had seen his primary doctor many times to find a solution but there was no success. The primary doctor then referred Ted to a neurologist. The neurologist then prescribed pain medication which aided to a certain extent but not help completely. Ted then began taking the tea in early 2015. After taking the tea remedy for a period of 2 months, he noted a significant improvement on his condition. His pain level reduced by approximately 80% and this has been without the aid of the prescribed pain medication. Ted feels much better now and is back to his wood working hobby where his joints feel fully functional.

Ramon S. a resident of the state of Illinois, USA, was diagnosed with acute bronchitis in 1994. Since then, every winter, it had been difficult with many ailments including severe cough, sore throat, fever and body aches. His primary doctor prescribed medication to ease his pain and suffering. With the prescribed medication, he felt a little better but had to constantly take such pharma medication year after year. He then started to take a natural tea remedy of the present invention, one teaspoon every morning with coffee. Just weeks after taking the natural tea product, he felt relieved and healed from his acute bronchitis condition. He has not taken any prescribed medication for this condition for many years; he just has continued to take the natural tea remedy of the present invention.

Lorenzo S. a resident of the state of Illinois, USA, was diagnosed with gout attacks, a painful inflammation of the joints, typically caused by uric acid in the blood. Lorenzo had been with this gout condition since 2013. His primary doctor prescribed daily medication but the gout attacks continued to persist. In July of 2014, Lorenzo began to take a natural tea remedy of the present invention (one spoonful of the tea concentrate with a glass of water per day). Three weeks after consuming the tea, he felt relieved of his gout condition, no significant pain and swelling returned. He now feels much better and is able to go about his daily routine without any fear of the gout attacks.

Agnes G. S. a resident of Clarin, Misamis Occidental, Philippines, suffered from chronic headaches. She was getting daily headaches to the point where she could not sleep well and had lost her appetite. She was dealing with these conditions by taking over the counter pain killers. The fatigue kept on getting worse with time. These issues then lead to suffer from anxiety problems. She then started to take the Sagrado Natural Team Remedy 3-4 times per day and after a few weeks, she obtain relief from the issues listed above. The anxiety issues have greatly demised and the headache problems have fully eradicated.

Rachel M. O. a resident of Oroquieta City, Misamis Occidental, Philippines, had been suffering from chest pain, which then led to a lump on her chest leading to breast cancer as diagnosed in February 2017. The doctor wanted to operate her breasts but a friend of Rachel suggested she take the Sagrado Natural Tea Remedy. Agnes started to take the remedy 3 times per day and after several months of taking this remedy (3 months), the chest pain was gone, she was sleeping better and most importantly, her lump on her chest was gone.

Jonalyn A. N. a resident of Pana-on, Misamis Occidental, Philippines, suffered from dizziness which then caused frequent headaches. At first, Jonalyn was taking Biogesic for pain relief, but most of the time this particular medication did not cure her conditions. A friend of the family recommended she takes the Sagrado Natural Tea Remedy. In July 2017 Jonalyn started to drink the tea remedy 3 times per day. After just a few week of drinking the tea, she stated to experience positive effects, headaches went away. She also testified that the Sagrado Natural Tea Remedy did not have any side effects as did the Biogesic she was originally taken.

Canilo A. D. C. a resident of Oroquieta City, Misamis Occidental, Philippines, had a drinking problem with liquor. Due to so much drinking, it led to peptic ulcers which caused upset stomach issues, difficulty sleeping and weight loss. The doctor prescribed which did not help much and caused side effects of vomiting and loss of appetite. In January 2017 a friend of Canilo recommended he drink the Sagrado Natural Tea Remedy. Canilo then took the tea remedy 3 times per day and after several weeks he felt great improvements. The abdominal pain was gone, the appetite came back. Canilo continues to take the tea remedy in a regular basis and has helped him get back to his normal routine and he has been sleeping well since then.

Luzminda M. D. C a resident of Oroquieta City, Misamis Occidental, Philippines, had been suffering from severe muscular pain to the point were she could hardly walk. This condition caused Luzminda to get very irritated and stressed which led to seeing a local doctor. The doctor prescribed pain medication but had little positive effect and caused other issues with she lost her appetites and also obtained insomnia. A friend of Luzminda convinced her to take the Sagrado Natural Tea Remedy. She started to take the tea remedy 3 times per day for three months starting in February 2017. After taking the tea remedy just for a few weeks, she obtained positive effects, the muscle pain went away, and she is eating well and continues to take the tea to date just as general maintenance.

Tessie D. A. a resident of Plaridel City, Misamis Occidental, Philippines, was diagnosed with breast cancer by her physician. Shortly after, her doctor chemo medication and radiation. But due to financial trouble, Tessie could not afford to pay for the radiation treatment. A friend of the family convinced Tessie to take the Sagrado Natural Tea Remedy. She started taking the tea remedy 3 times per day, and after two weeks, she found positive effects, the pain has greatly subsid, and her chest cancer cyst was gone. She continues to take the tea remedy as part of her normal routine because it make her feel comfortable, helps with a good appetite and good sleep.

Ponciano D. B. A a resident of Plaridel City, Misamis Occidental, Philippines, had been officially paralyzed since 2016 due to high blood pressure issues which had led to a stroke. His body was in poor health and very weak due to his paralysis. Ponciano was taking many over the counter medications to help him with his illness but made him highly irritable and had very little appetite. A friend suggested he take the Sagrado Natural Tea Remedy. He started to take the tea remedy 3 times per day in 2016. Several weeks later he experienced great benefits by getting relieve from headaches, dizziness and stroke symptoms. More impressively, Ponciano can now move fully on his own. He felt so conformable with the tea remedy that to date, he continues to take the tea on a regular basis.

Lorna B. resident of Oroquieta City, Misamis Occidental, Philippines, suffered from severe chest pain and back pain. The pain made her lost the appetite which then led to weight loss. Lorna ask her daughter in May of 2017, to take her to the doctor. The doctor prescribe some antibiotics and pain killers. Unfortunately, the pain killers prescribed did not help alleviate his pain. A friend of Lorna convince her to take the Sagrado Natural Tea Remedy. Lorna started to take the tea remedy 3 times per day. Weeks after taking the tea remedy, Lorna felt well and her chest pain and back pain went away.

Violeta M. A. a resident of Oroquieta City, Misamis Occidental, Philippines, whom is of advanced age, whom ate fatty food, junk food, which in January 2017 led to prone urinary tract infections causing disruptions with her life and high stress levels. After going to see her doctor, she was prescribed with several medications to alleviate her symptoms. Shortly after, a relative of Violeta informed her of the Sagrado Natural Tea Remedy. Violeta started to take the tea remedy 3 times per day. After taking the tea remedy for several weeks, the urinary tract infections greatly lessened and she then felt good, less stressful.

Jimmy M. M. a resident of Oroquieta City, Misamis Occidental, Philippines, had been suffering from prone headaches and constant coughing. Coughing and headaches were occurring every morning to the point where it caused loss of appetite and loss of weight. He went to his doctor and doctor prescribed medication for his conditions. The symptoms did not subside. Then a friend of Jimmy informed him about the Sagrado Natural Tea Remedy. Jimmy started to take the tea remedy in March of 2017 and took it 2 times per day. Just weeks into taking the tea remedy, Jimmy started to feel better to the point where the headaches and cough was eliminated without the help of the doctor's medications as he did not take them. He now continues to take the tea remedy and is also helping with eating and sleeping well Romeo O. a resident of Oroquieta City, Misamis Occidental, Philippines, has been suffering from a lump or growth in his stomach, it became so big that caused difficulty with breathing normally leading into getting dizzy. The growth was there for several months and after so long, in June 2017, Romeo's wife investigated what to do and she learned about the Sagrado Natural Tea Remedy. Romeo was then able to take the tea remedy on a daily basis and after taking such tea for one month the lump in his stomach greatly reduced to the point where the issues with breathing and dizziness subside. He is now back leaving a normal life.

Dionisio C. A. a resident of Zamboanga del Norte, Philippines, has been suffering from severe back pain which caused a sinda condition which interfere which his daily activities including going to work. Dionisio went to his regular doctor at a local clinic and was prescribed with pain medication and antibiotics. He was taking such medications for a period of 2 months obtained several side effects which caused other problems. After minimal improvement, Dionisio was talking with a neighbor whom had a cousin in the province of Misamis Occidental and recommended him to take the Sagrado Natural Tea Remedy. Dionisio started to take the tea remedy in February 2017, and after taking the tea remedy for a few weeks, he noticed improvements, and after four months, the illness, back pain, and dizziness was fully eradicated.

Alma O. a resident of Oroquieta City, Misamis Occidental, Philippines, was suffering from constant headaches, which caused dizziness, loss of appetite which then negatively affected his condition to go to work. Her husband had heard about the Sagrado Natural Tea Remedy. He was able to obtain such tea remedy for Alma and after just one week of consumption on a daily basis, the headaches had gone away as well as the other symptoms. Since then, Alma is back to her normal routine including back to work.

Marie Claire M. D. C. a resident of Oraquieta City, Misamis Occidental, Philippines, had a lump on her chest. She went to her physician and confirmed she had a cancerous cyst on one of her breasts and advised to be operated. The cyst had been there for almost 2 moths which caused severe pain and lead to difficulty sleeping, stress and eventually led to a nervous breakdown. She was so depressed she refused to go back to the doctor and take the medications the doctor had prescribed her. She was losing a lot of weight. Through some neighbors, she heard of this reliable and natural source to cure her condition known as the Sagrado Natural Tea Remedy. After taking the tea remedy for just a period of two months, 4 times per day, she noticed that the lump and pain on her chest had greatly diminished, and nowadays, the tea remedy had such a positive effect that her cancer has been cured.

Verbal First Hand Testimonials to the Inventor of the Sagrado Natural Tea Remedy:

Gloria R. a resident of the state of Illinois, USA, was diagnosed with a cancerous goiter on her throat. After being under a doctor's care for several months, the goiter became more severe and enlarged. In June 2014, she began to take a natural tea remedy of the present invention (one tablespoon per day every morning). After consuming the tea remedy for a period of weeks, the goiter was destroyed. She then went back to her doctor in the fall of 2014 and the doctor witnessed her goiter being gone. Cancer is in remission, and Gloria is now back to her normal life.

Mrs. Ortiz, resident of the state of Illinois had a severe diabetic wound on her right ankle which eventually was infected with gangrene. In or about November of 2004, her primary doctor and endocrinologist recommended she gets an amputation of her lower leg. She then started to take natural tea remedy of the present invention (the ashes of the 7 plant materials prepared by the inventor, applying them topically over the infected foot areas on a daily basis). Two months after following the procedure from the inventor, her wound closed, dried up and completely healed. Today, she walks normally with both feet intact without the need of amputation.

Andy F. a resident of the state of Illinois, USA, was diagnosed with cancer of the skin, on his face, primarily around his nose area. In May 2016, he started to take a natural tea remedy of the present invention (one tablespoon per day every morning) he also applied with a cotton swab topically some of the tea concentrate directly on to his face in the affected areas. Two weeks after following this procedure, Andy's cancer had greatly diminished, the redness on his face was gone and now he is back to his normal life.

Mr. Michalowicz a resident of the state of Illinois, USA, was diagnosed with cancer of the tongue in November 2004. The doctors had talked to him about his severe condition and informed him he had only a few months to live. He then started to consume a natural tea remedy of the present invention (three times per day, one tablespoon each time). In addition, he was administered to apply the ashes of the 7 plant materials provided by the inventor directly on to the affected tongue area. Weeks after following this procedure, the tongue had completely healed, the cancer went in to remission. Many years later he is feeling good and living a normal life.

Reina S. a resident of the state Illinois, USA, was diagnosed with mammary cancer which led into full mastectomy for the removal of both of her breasts. After the surgery the doctors informed Reina the cancer had spread and she had only months to live. In April 2016, she started consuming the tea (three times per day, one tablespoon each time). Only a few weeks after taking the tea, her condition greatly improved, her hair grew back, cancer is in remission and today, she is back to her normal life.

Agapito A. a resident of the state of Illinois, USA, had a severe case of rheumatoid arthritis. His condition was so intense that she started to use a cane and then was eventually confined to a wheelchair since she could not walk on his own anymore. In or about June 2005, he started to consume a natural tea remedy of the present invention (three times per day one tablespoon each time). Only two months after taking the tea remedy, he started to feel much better, his condition greatly improved and today; he walks without the need of a cane or a wheelchair.

Alicia V. a resident of the state of Illinois, USA, had a very severe case of arthritis of her extremities, including arms and legs. This condition limited her to function properly and attain to her family needs and her own needs. In October of 2014, she started to take a natural tea remedy of the present invention (one tablespoon, one time per day). Just two weeks after taking the tea remedy, she reported of feeling significantly better and estimated that approximately 80% of her pain and limitation has been removed. Since then, she continues to take the tea remedy just as maintenance of her overall health and feels very mobile and back to her normal self before the arthritis started.

These testimonials were all voluntary and are just a few examples obtained from several friends and family members of the inventor. Since the original creation of such tea remedy, several dozen people have greatly benefited from the tea remedy. This tea remedy is an all-natural product which has multiple properties for preventing various ailments as describe above. In most cases, the tea concentrate is consumed orally but in a few instances, depending on the ailment and condition, the administration has been topically applied with the tea concentrate or with the ashes of the plant ingredients. In general, the tea is prepared from 7 ingredients procured from the Philippines by the inventor via several relatives whom still live in the area. Native Indians have practiced such procedures from natural plant resources for centuries. Such natural teas have aided with ailments of many types of health conditions. These types of natural tea remedies have been documented to exhibit diverse properties that function by removing from the human body toxic compounds which initiate disease and unbalances. The Sagrado Natural Team Remedy offers diverse ingredient formulation which is able to maintain several of the main organ systems in proper health. One aspect of this tea is the unique level of naturally occurring flavonoids such as catechins with combination of the same have been known to increase the natural immunity of the body and increase the disease fighting properties in particular against cancer. This is done by elevating the level of antioxidants which promote good blood circulation and eliminate free radicals found in the body. By combining these specific 7 tree ingredients at the ratios described in this invention, it was captured via the above testimonials that it has offered many benefits to people whom might not obtained what they were seeking from their primary doctors via standard pharma medications or at least without any know side effects.

Traditional herbal medicine from various parts of the world including those of the Philippines as just described, have been well documented for many decades, perhaps centuries of combating aliments of various types. New interest continues to arise from people whom have not succeeded with traditional pharma medicines. It is with great faith and evidence, including common knowledge passed from several generations by native ancestors, including tribes from the Philippines that have sparked the idea to the inventor to combine such unique ingredients and create the Sagrado Natural Tea Remedy to offer an effective, natural therapeutic alternative.

I claim:

1. A mixture comprising tree branch ingredients from tree branch materials comprising:
   (i) *Celastrus orbiculatus,*
   (ii) *Myristica philippensis,*
   (iii) *Pterocarpus indicus,*
   (iv) *Ficus codatula* var. *sericea,*
   (v) *Corida dichotoma,*
   (vi) *Caesalpinia sappan,* and
   (vii) *Dracontomelon dao,*
   wherein the mixture is prepared by chopping the tree branch materials to form chopped tree branch material wherein the chopped tree branch material is formed into the mixture by forming ashes by burning the chopped tree branch material and forming a topical ointment from the ashes of the chopped tree branch material.

2. The mixture of claim 1 with the tree branch ingredients specified in claim 1 at amounts in the range of 1% to 50% by weight of each of the tree branch materials.

3. The mixture of claim 1 with the tree branch ingredients specified in claim 1 at amounts in the range of 3% to 30% by weight of each of the tree branch materials.

4. The mixture of claim 1 with the tree branch ingredients specified in claim 1 at amounts in the range of 5% to 20% by weight of each of the tree branch materials.

5. A method of making a tea mixture comprising:
   providing tree branch materials, wherein the tree branch materials comprise (i) *Celastrus orbiculatus,* (ii) *Myristica philippensis,* (iii) *Pterocarpus indicus,* (iv) *Ficus codatula* var. *sericea,* (v) *Corida dichotoma,* (vi) *Caesalpinia sappan,* (vii) *Dracontomelon dao;*
   preparing wood chips of the tree branch materials;
   drying the wood chips;
   adding water to the dried wood chips to form a water and wood chip mixture; and
   boiling the water and extracting a tea from the water and wood chip mixture.

6. The method of claim 5 further wherein the wood chips of the tree branch material comprise between about 1 and 80% by weight of each of the tree branch materials.

7. The method of claim 5 wherein the wood chips of the tree branch material comprise between about 3 and 50% by weight of each of the tree branch materials.

8. The method of claim 5 wherein the wood chips of the tree branch material comprise between about 5 and 20% by weight of each of the tree branch materials.

9. The method of claim 5 further comprising the step of: preparing a beverage from the tea.

10. The method of claim 5 further comprising the step of: preparing an ointment from the tea.

11. A method of making an ointment mixture comprising:
    providing tree branch materials, wherein the tree branch materials comprise (i) *Celastrus orbiculatus,* (ii) *Myristica philippensis,* (iii) *Pterocarpus indicus,* (iv) *Ficus codatula* var. *sericea,* (v) *Corida dichotoma,* (vi) *Caesalpinia sappan,* (vii) *Dracontomelon dao;* preparing wood chips of the tree branch materials;

drying the wood chips;

forming an ash of the wood chips by burning the wood chips; and forming an ointment from the ash of the wood chips.

12. The method of claim 11 wherein the wood chips of the tree branch material comprise between about 1 and 80% by weight of each of the tree branch materials.

13. The method of claim 11 wherein the wood chips of the tree branch material comprise between about 3 and 50% by weight of each of the tree branch materials.

* * * * *